United States Patent [19]

McClure

[11] 4,267,056
[45] May 12, 1981

[54] SAMPLE PREPARATION APPARATUS AND PROCESS FOR THE USE THEREOF

[75] Inventor: Thomas D. McClure, Northglenn, Colo.

[73] Assignee: Johns-Manville Corporation, Denver, Colo.

[21] Appl. No.: 27,332

[22] Filed: Apr. 5, 1979

[51] Int. Cl.³ .............................................. B01D 15/08
[52] U.S. Cl. ................... 210/678; 210/257.1; 210/284; 23/230 M; 422/70
[58] Field of Search ............... 422/69, 70; 23/232 C, 23/230 M; 210/692, 674, 689, 691, 678, 257.1, 259, 269, 278, 284, 287, 290, 30 R, 32, 40, 41, 31 C

[56] References Cited

U.S. PATENT DOCUMENTS

| | | | |
|---|---|---|---|
| 4,009,005 | 2/1977 | Johnson | 422/71 |
| 4,047,892 | 9/1977 | Fuller | 23/232 C |
| 4,083,690 | 4/1978 | Inoue | 23/230 M |

FOREIGN PATENT DOCUMENTS 42-240  1/1967  Japan .................................. 23/230 M Primary Examiner—William F. Smith
Attorney, Agent, or Firm—Robert M. Krone; Joseph J. Kelly

[57] ABSTRACT

An apparatus and its method of use are described for the preparation of samples for organic material analysis, especially for gas chromatographic analysis. The samples in question are samples of organic materials (usually in trace quantities) which have originally been dissolved in water. In the process and apparatus of the present invention each sample is initially transferred to an adsorbent material from which it is in turn transferred to an organic solvent (which may be subsequently dried) and collected and from which the chromatographic analysis sample can later be withdrawn.

12 Claims, 2 Drawing Figures

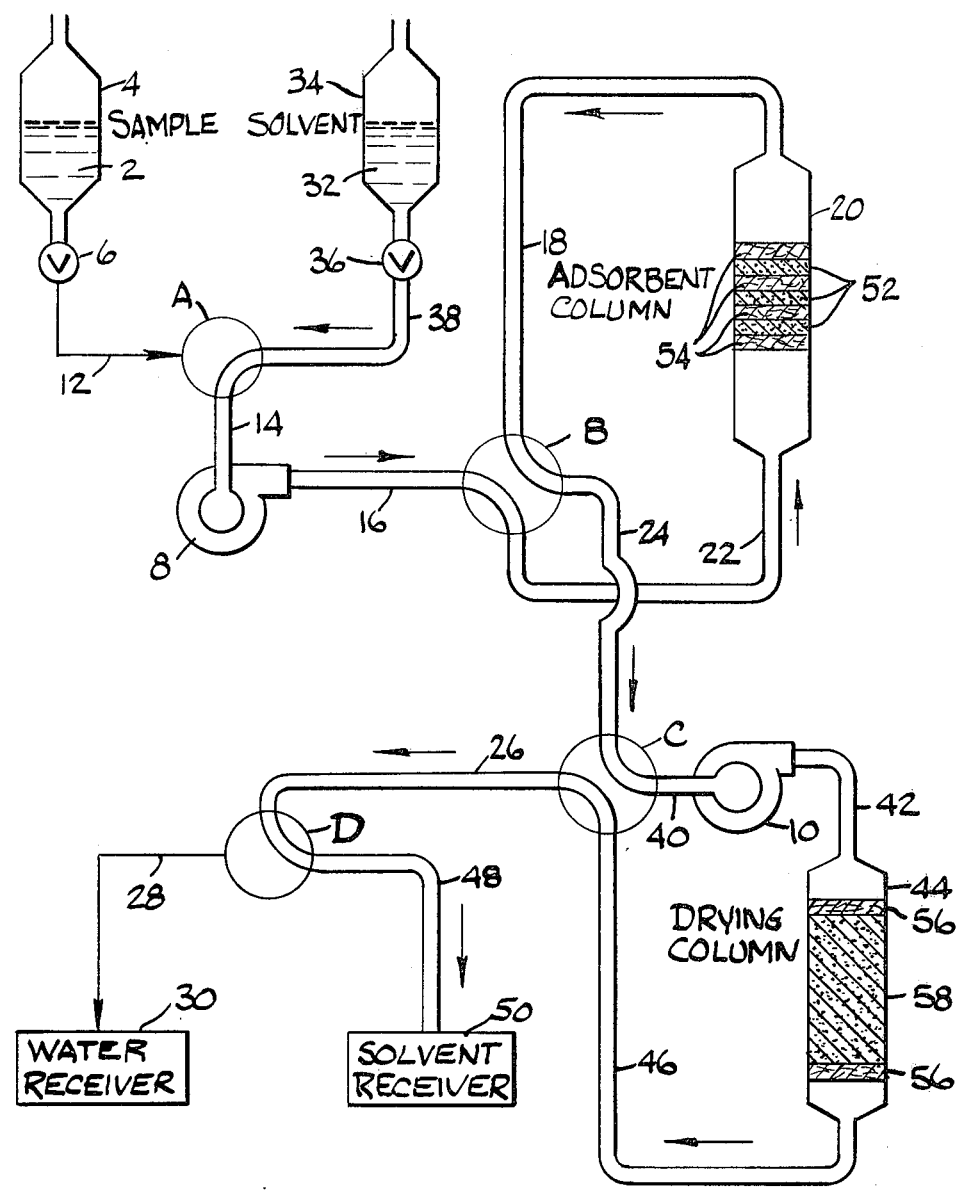

SAMPLE PREPARATION APPARATUS AND PROCESS FOR THE USE THEREOF

TECHNICAL FIELD

The invention herein relates to apparatus for the preparation of samples for analysis for small amounts of organic materials.

BACKGROUND OF THE PRIOR ART

It has become increasingly important in recent years to be able to analyze water samples for the presence, usually in trace amounts, of various organic materials (particularly those labeled as "priority pollutants") and to be able to identify the particular organic materials which are present in the water. Such detection and identification of organic materials is important, for instance, in assuring the safety of municipal potable water supplies. It is also important in the monitoring of waste discharges into sewage systems and waterways from various industrial processes.

Chromatographic analysis by means of gas chromatography is a well known and effective way of detecting and identifying very small amounts of organic materials. Gas chromatography systems, however, have the serious limitation that they are normally unable to handle water samples. Thus, means must be found to transfer the organic materials from the original water samples to solvent carriers from which chromatography samples can be obtained. Transfer systems used in the past, however, have a number of disadvantages, with one of the most common and serious being that the rate of transfer is cumbersome and/or extremely slow, thus making analysis sample preparation a tedious procedure. Other disadvantages of the various prior art transfer systems include their complexity, high volume of solvent usage, lack of accuracy, poor degree of recovery and/or expense.

It would therefore be particularly desirable to have a simple transfer system for the separation and concentration of organic materials from water samples, which system would enable the user to rapidly and completely transfer the organic materials from the water sample to a suitable organic solvent carrier. Such a system would advantageously also enable the user to prepare large numbers of samples in a relatively short time and with minimal cost and material usage.

BRIEF SUMMARY OF THE INVENTION

The invention herein includes apparatus comprising a system particularly useful for the separation and concentration of organic materials from water samples, which apparatus comprises: at least one sample reservoir and at least one solvent reservoir, each having a fluid conduit leading therefrom; at least one adsorbent column containing at least one layer of adsorbent material and having fluid conduits at opposite ends thereof; at least one water receiver and at least one solvent receiver, each having a fluid conduit leading thereto; first valve means to alternately connect each of the fluid conduits of the reservoirs to a fluid conduit of the adsorbent column, with the fluid conduit of the adsorbent column to which the first valve means is at any given time connecting one of the reservoirs being at that time the inlet fluid conduit of the adsorbent column and the other of the fluid conduits of the adsorbent column being at that time the outlet fluid conduit of the adsorbent column; and second valve means to alternately connect each of the fluid conduits of the receivers to the outlet fluid conduit of the adsorbent column.

In a preferred embodiment, the apparatus further comprises at least one drying column containing at least one layer of drying material and having respectively inlet and outlet fluid conduits at opposite ends thereof, the drying column being interposed between the adsorbent column and the second valve means and with the outlet fluid conduit of the adsorbent column connected to the inlet fluid conduit of the drying column and the outlet fluid conduit of the drying column connected to the second valve means.

The invention also comprises a process, utilizing the above apparatus, for separating organic material from water and concentrating the organic material in a solvent from which an analysis sample can be obtained, which process comprises passing the quantity of water containing the organic material through an adsorbent material to remove the organic material from the water by adsorption onto the adsorbent material; removing the water from the vicinity of the adsorbent; transferring the organic material from the adsorbent material to a solvent for the organic material by passage of the solvent through the adsorbent material; and, in a preferred embodiment, drying the organic-material-containing solvent for subsequent introduction into an analysis system for detection and identification of the organic material.

BRIEF DESCRIPTION OF THE DRAWINGS

FIGS. 1 and 2 are both schematic diagrams of the process of the present invention illustrating the apparatus used therein. FIG. 1 shows the flow path of the water sample through the apparatus, while FIG. 2 shows the flow path of the organic solvent.

DETAILED DESCRIPTION OF THE INVENTION

Figure 1:
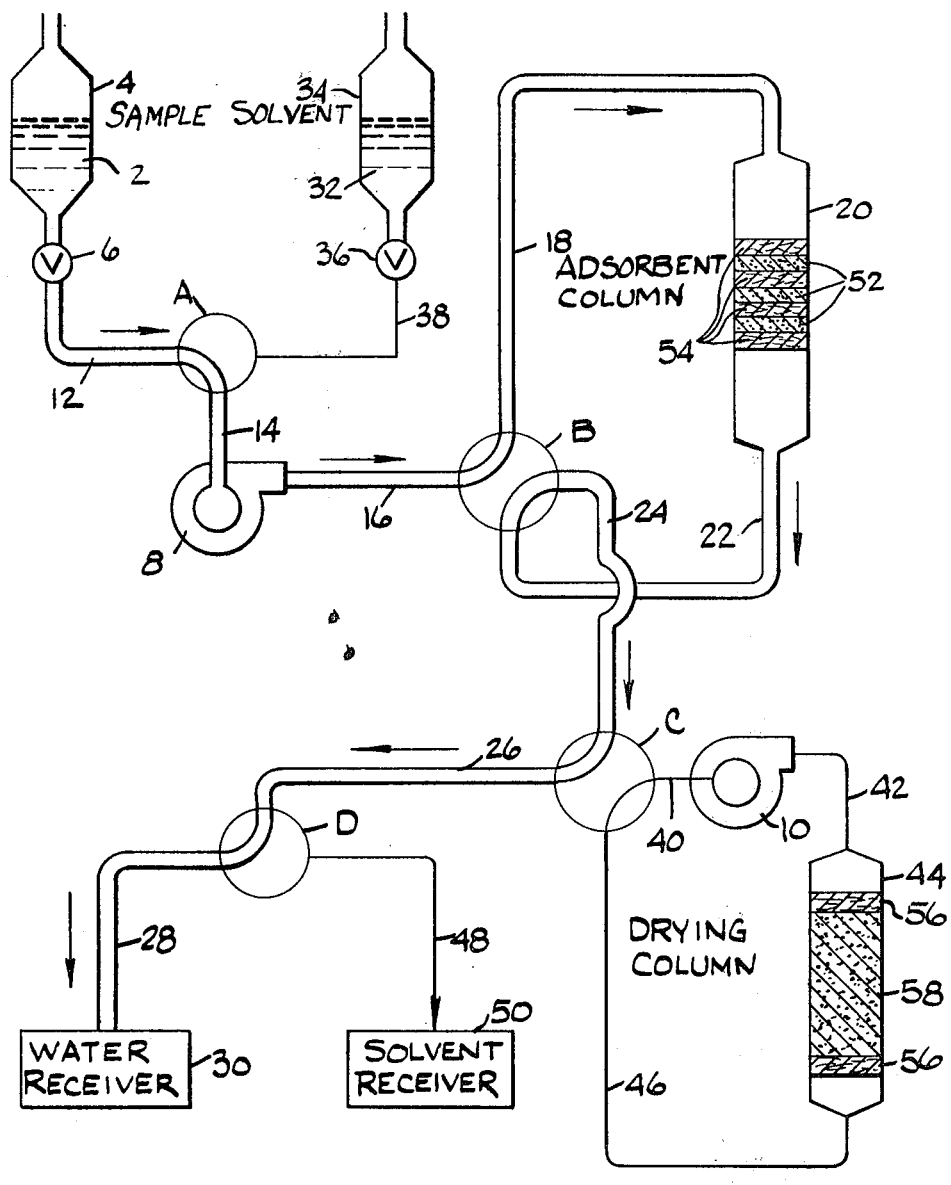

The apparatus of the invention herein and its method of use will be best understood by reference to the attached drawings.

FIG. 1 illustrates the apparatus of this invention assembled and aligned so as to effect the first portion of the process of this invention, i.e., extraction or separation from a "contaminated" water sample 2 of at least certain of the organic contaminants believed to be in that sample. (The term "contaminated" will be used herein for brevity merely to indicate that the water sample contains the organic materials of interest. The use of the term is not meant to imply that the organic materials are necessarily unwanted, harmful, waste or otherwise undesirable. While the organic materials may in fact be, for instance, noxious or harmful (as, e.g., the aforementioned "priority pollutants" in potable water), they may equally be materials (such as certain drugs) which are very desirable to separate from the water and retain for their own end uses.) The contaminated water sample 2 is housed in sample reservoir 4. Due to the versatility of the present system, any convenient size of water sample may be used. Excellent results can be obtained utilizing sample sizes as small as one milliliter. Prior to beginning of the extraction portion of the process of use, the sample reservoir 4 is isolated from the remainder of the system by closure of valve 6, which is typically a stopcock when the apparatus is of laboratory scale.

(For convenience in understanding of the process of use of this invention, the diagrams of FIGS. 1 and 2 have been drawn to indicate the conduits which define the flow path of the particular material in question by two parallel lines. Flow paths or conduits indicated by single lines are those which are not being used during the particular portion of the process under consideration.)

At the beginning of the extraction portion of the process the valves A, B, C and D are aligned as shown in FIG. 1. When valve 6 is opened, peristaltic pump 8 is started, causing the contaminated water sample 2 to flow out of reservoir 4 through line 12, valve A, line 14, pump 8, line 16, valve B, and line 18 to adsorbent column 20. This alignment of valve B defines line 18 as the "inlet conduit" of adsorption column 20 during this phase of the system's operation, and line 22 thus simultaneously becomes defined as the "outlet conduit." The alternate alignment of valve B (FIG. 2) will reverse the "inlet" and "outlet" designations. In adsorbent column 20 (which will be described below) the organic materials under investigation are separated or extracted from the water as the latter passes through the adsorbent material in the column. The organic contaminants of interest stay adsorbed on the adsorbent material while the water flows through and out of column 20 through line 22. The water now continues through the second passage of valve B and on through line 24, valve C, line 26, valve D, and line 28 to water receiver 30. The water sample may then be discarded, retained for further analysis or otherwise dealt with as desired. Thus at the end of the extraction portion of the process the organic materials to be investigated have been removed from the water sample and are adsorbed on the adsorbent material in column 20. It is desirable after the water has flowed through the system to continue the operation of pump 8 for a period of time such as several minutes to provide as much forced air drying of the system as possible.

In the concentration portion of the process both pumps 8 and 10 are operated and valves A, B, C and D are aligned as shown in FIG. 2. The organic solvent 32 is initially contained in solvent reservoir 34. The particular solvent chosen will of course be one which has sufficient ability to dissolve the trace organic materials whose presence is being investigated during the solvent's residence time period in the adsorbent column. When the concentration portion of the process is started, valve 36 (which like valve 6 is normally a stopcock when the apparatus is of laboratory scale) is opened and the solvent 32 flows through line 38, valve A, line 14, pump 8, line 16, valve B and line 22 to adsorbent column 20. In the preferred embodiment shown, the solvent thus flows through column 20 in a countercurrent direction as compared to the previous flow of the water, thus, as noted above, reversing the "inlet" and "outlet" designations of lines 18 and 22. This counter-current flow materially aids in the removal of the trace organics from the adsorbent by the solvent. Cocurrent flow could be used, however, if desired, by aligning valve B as in FIG. 1. Normally, with the proper choice of solvent and adsorbent, essentially complete transfer of the organic materials from the adsorbent into the solvent will be obtained.

The solvent now containing the dissolved organic materials then flows through line 18 (in the preferred counter-current mode shown in FIG. 2; line 22 in cocurrent flow), the second passage of valve B, line 24, valve C, line 40, pump 10 and line 42 to drying column 44. The use of drying column 44 is preferred because the system will contain small amounts of residual water from the passage of the water sample, with water being both adsorbed in the adsorbent column and also adhering to the inside of the various lines and valves through which the water has passed. This residual water is commonly picked up in the solvent and must be removed by drying column 44 to place the sample in the optimum condition for subsequent chromatographic analysis. The nature of the materials in the drying column will be described below. In some cases it may be possible to bypass the drying operation and pass the solvent containing the organic materials straight through line 24, valve C (aligned as in FIG. 1), line 26, valve D and line 48 to solvent reservoir 50. This may, for instance, be possible when the particular solvent being used is very hydrophobic and thus has a very low affinity for water pick-up from the system.

The better practice, however, is to dry all solvents following their passage through adsorbent column 20 to insure that, no matter how hydrophobic the solvent, any water present will be removed. Therefore in the preferred embodiment, the solvent containing the organic materials passes through column 44 and flows out through line 46, the second passage of valve C, line 26, valve D, and line 48 to solvent receiver 50. Solvent receiver 50 may be any kind of desired container from which samples for subsequent chromatographic analysis can later be withdrawn. Analysis sample size and any further sample workup such as enhancement of the organic material concentration by removal of some of the solvent prior to analysis can be performed through conventional techniques.

In the apparatus as shown schematically in the diagrams valves A and D are three-way valves while valves B and C are four-way valves. The various flow lines may be constructed of materials such as glass tubing, PTFE tubing, copper tubing or the like. This apparatus will normally find its major use in laboratory sample preparations, and therefore the various flow lines will be composed of laboratory scale tubing sizes. However, it is possible for the system of this invention to be used in substantially larger scales. In the latter cases the flow lines would of course be of appropriately larger sizes, and therefore use of the term "tubing" is not to be construed as limiting in any manner.

Adsorbent column 20 may be packed with any adsorbent material which will act to adsorb the particular organic materials which are under investigation. A wide variety of adsorbent materials such as diatomite and various resinous adsorbents may be used. A large number of such materials are available commercially, including those sold under the trademarks "CELITE" and "CHROMOSORB" by Johns-Manville Corporation. The adsorbing properties of each of these commercial materials and the various types of organic materials for which each is best suited are described in the literature and commercial information available from the various manufacturers. The choice of the particular adsorbent or combination of adsorbents used will naturally depend on the specific types of organic materials which are sought to be removed from the water stream, on the nature of the particular solvent to be used to remove the organic materials from the adsorbent, the temperature and flow rate at which the apparatus is to be operated, and the other operating parameters which will be well understood by those skilled in the art of adsorption and desorption. In most cases the adsorbent materials are in finely divided granular form and it will be found convenient to arrange the adsorbent in one or more layers separated by supporting material such as glass fiber wool. In a particular application good results with a wide variety of organic materials have been found by using an adsorbent column packed with several individual layers 52 of a mixture of "CELITE 503" diatomite and "CHROMOSORB 106" support material separated and supported by alternating layers of glass fiber wool 54. Each layer 52 may comprise a separate type of adsorbent, or two or more layers may have the same adsorbent. Adsorbents may also be mixed in an individual layer.

Drying column 44 may be packed with any convenient hydrophilic drying material. It is preferred to use a material which has a much higher affinity for water than for organic materials so that the entering organic solvent, containing the organic materials and the residual water, can pass through the drying column with substantially complete removal of water but with minimal depletion of either the solvent or the organic materials. Many of the common drying materials are also in finely divided granular form and therefore they too can be conveniently layered and supported by materials such glass wool 56. In a typical application good results have been obtained using as the drying material 58 a commercial anhydrous calcium sulfate drying agent sold under the trademark "Drierite" by W. A. Hammond Drierite Company.

As a typical example of the apparatus of this invention and the process of its use, a number of water samples each containing 1 ppm of trichloromethane were prepared. Sample volumes ranged from 25 to 500 ml. Each sample was run individually through a laboratory scale system of this invention. Total time for separation and concentration of the trichloromethane from each sample was in the range of 7 to 10 minutes, and the trichloromethane extraction yield was in all cases on the order of 95% or better. By comparison, prior art equipment and processes cannot achieve this combination of speed and high yield. Those prior art systems which have high yields commonly require 1 to 3 hours to process a sample, while faster systems commonly have low yields.

This system also has other advantages not found in many prior art systems. It lends itself readily to automation by using automatic sequencing controls for valves A, B, C and D. The operator need only switch sample reservoir 4 for each new sample while the concentration portion of the process for the previous sample is underway and switch solvent receiver 50 for each sample while the extraction portion of the process is underway for that sample. It would also be possible to provide for multiple sampling using a manifold arrangement with valve A so that a series of prefilled sample reservoirs 4, 4', 4'', etc. (not shown) could be connected sequentially to the system. Similarly, a substantial decrease in sample preparation times and a related increase in the number of samples prepared could be obtained by use of multiple adsorption columns 20, 20', 20'', etc. (not shown) connected by a manifold arrangement to valve B.

It will also be evident that while this system is intended for and described in terms of preparation of samples for gas chromatography analysis, it will be equally useful whenever separation and concentration of small amounts of organic materials from water are required in a process for other analyses or for any similar type of use.

STATEMENT OF INDUSTRIAL APPLICATION

The invention herein finds particular application in the preparation of samples of trace organic materials for analysis. It is most particularly useful for preparation of samples for analysis by gas chromatography.

I claim:

1. Apparatus for the preparation of samples for chromatographic analysis, which samples comprise organic materials initially present in a quantity of water, said apparatus comprising:
    (a) at least one sample reservoir and at least one solvent reservoir, each having a fluid conduit leading therefrom;
    (b) at least one adsorbent column containing at least one layer of adsorbent material and having fluid conduits at opposite ends thereof, with the fluid conduit of said adsorbent column to which a first valve means is at any given time connecting one of said reservoirs being at that time the inlet fluid conduit of said adsorbent column and the other fluid conduit of said adsorbent column being at that time the outlet fluid conduit of said adsorbent column;
    (c) at least one water receiver and at least one solvent receiver, each having a fluid conduit leading thereto;
    (d) said first valve means to alternately connect each of said fluid conduits of said reservoirs to said inlet fluid conduit of said adsorbent column;
    (e) second valve means to alternately connect each of said fluid conduits of said receivers to said outlet fluid conduit of said adsorbent column; and
    (f) at least one drying column containing at least one layer of drying material and having respectively inlet and outlet fluid conduits at opposite ends thereof, said drying column being interposed between said adsorbent column and said second valve means and with said outlet fluid conduit of said adsorbent column connected to said inlet fluid conduit of said drying column and said outlet fluid conduit of said drying column connected to said second valve means.

2. Apparatus as in claim 1 further comprising:
    (g) third valve means to connect said outlet fluid conduit of said adsorbent column alternately to said inlet fluid conduit of said drying column or directly to said second valve means.

3. Apparatus as in claims 1 or 2 further comprising:
    (h) fourth valve means to direct the flow of fluid from said reservoirs alternately into either one or the other of said fluid conduits of said adsorption column.

4. Apparatus as in claim 3 further comprising:
    (i) first pump means disposed in at least one of said fluid conduits of said adsorbent column.

5. Apparatus as in claim 4 further comprising:
    (j) second pump means disposed in at least one of said fluid conduits of said drying column.

6. A process for the preparation of a sample for analysis utilizing apparatus as in claim 1, which sample comprises organic material initially present in a quantity of water, said process comprising:
    (a) passing said quantity of water containing said organic material through said adsorbent material to remove said organic material from said water by adsorption onto said adsorbent material;

(b) removing said quantity of water from the vicinity of said adsorbent material;

(c) transferring said organic material from said adsorbent material to said solvent from said organic material by passage of said solvent through said adsorbent material; and (d) drying said organic-material-containing solvent for subsequent introduction into an analysis system for detection and identification of said organic materials.

7. A process as in claim 6 wherein said solvent is passed through said adsorbent material in a direction counter-current to the direction of passage of said water.

8. A process for the preparation of a sample for chromatographic analysis utilizing apparatus as in claim 1, which sample comprises organic material initially present in a quantity of water, said process comprising:

(a) passing said quantity of water containing said organic material from said sample reservoir to said adsorbent column;

(b) in said adsorbent column passing said quantity of water containing said organic material through at least one layer of said adsorbent material to transfer said organic material from said quantity of water to said adsorbent material;

(c) removing said quantity of water, from which said organic material has been transferred, from said adsorbent column and passing it to a water receiver;

(d) passing said solvent from said solvent reservoir to said adsorbent column;

(e) in said adsorbent column passing said solvent through said at least one layer of adsorbent material to transfer said organic material from said adsorbent material to said solvent; and (f) passing said solvent containing said organic material from said adsorbent column to a solvent receiver, from which samples for chromatographic analysis can be subsequently withdrawn.

9. A process as in claim 8 further comprising:

(g) in step (f), passing said solvent containing said organic material first to said drying column, and therein passing said solvent containing said organic material through at least one layer of a drying material wherein any water contained in said solvent is removed therefrom, and then passing said solvent containing said organic material on to said solvent reservoir.

10. A process as in claims 8 or 9 wherein said solvent is passed through said at least one layer of adsorbent material in a direction counter-current to the direction in which said quantity of water was previously passed through said at least one layer of adsorbent material.

11. A process as in claim 10 wherein there is a plurality of layers of said adsorbent material in said adsorbent column.

12. A process as in claim 11 wherein said plurality of layers of said adsorbent material contains a plurality of different individual types of adsorbent material.

* * * * *